United States Patent
Balaban

(10) Patent No.: US 6,723,365 B2
(45) Date of Patent: Apr. 20, 2004

(54) METHOD AND APPARATUS FOR CONTINUOUS FLOW REDUCTION OF MICROBIAL AND/OR ENZYMATIC ACTIVITY IN A LIQUID PRODUCT USING CARBON DIOXIDE

(75) Inventor: Murat O. Balaban, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/136,378

(22) Filed: May 2, 2002

(65) Prior Publication Data

US 2002/0122860 A1 Sep. 5, 2002

Related U.S. Application Data

(63) Continuation of application No. 09/613,714, filed on Jul. 11, 2000, now abandoned, which is a continuation-in-part of application No. 09/314,945, filed on May 20, 1999, now abandoned.
(60) Provisional application No. 60/095,967, filed on Aug. 10, 1998.

(51) Int. Cl.[7] .................................................. A23L 3/00
(52) U.S. Cl. ................... 426/521; 99/323.2; 426/330.5; 426/532
(58) Field of Search ................................ 426/521, 522, 426/330, 330.5, 532; 99/323.1, 323.2; 422/255

(56) References Cited

U.S. PATENT DOCUMENTS

| | | |
|---|---|---|
| 2,356,498 A | 8/1944 | Bargeboer |
| 2,569,217 A | 9/1951 | Bagdigian |
| 2,713,232 A | 7/1955 | Peterson |
| 2,838,403 A | 6/1958 | Notter |
| 2,967,777 A | 1/1961 | Grindrod |
| 3,442,660 A | 5/1969 | Shank |
| 3,477,856 A | 11/1969 | Schultz |
| 3,597,235 A | 8/1971 | Kramer |

(List continued on next page.)

FOREIGN PATENT DOCUMENTS

| | | |
|---|---|---|
| CA | 2280240 | 2/2000 |
| EP | 015184 | 12/1981 |
| EP | 812544 | 12/1997 |
| GB | 332641 | 7/1930 |
| JP | 3027268 | 2/1991 |
| WO | WO 89/02221 | 3/1989 |

OTHER PUBLICATIONS

Kamihira, M. et al., "Sterilization of microorganisms with supercritical carbon dioxide", Agricultural and Biological Chemistry, vol. 51, No. 2, pp. 407–412 (1987) (abstract).

(List continued on next page.)

*Primary Examiner*—George C. Yeung
(74) *Attorney, Agent, or Firm*—Dennis P. Clarke; Miles & Stockbridge P.C.

(57) ABSTRACT

A continuous method using gaseous carbon dioxide or a pressurized flow of liquefied carbon dioxide is described to reduce microbial and/or enzymatic activity in a liquid product. The carbon dioxide is combined with a pressurized flow of the liquid product, or the mixture is pressurized after the mixture is formed. The pressure and temperature in the flow regions are maintained at a level which is sufficient to keep the carbon dioxide in a continuous liquid state, but which does not freeze the liquid product. The pressurized mixture of the carbon dioxide and liquid product flows through a reaction zone for a sufficient time to reduce harmful microorganisms and/or inactivate enzymes and then enters one or more expansion stages wherein the pressure of the mixture flow is sufficiently decreased to vaporize the carbon dioxide for separation from the liquid product. If necessary, heat is applied in at least one of the expansion stages to prevent a freezing of the mixture.

47 Claims, 2 Drawing Sheets

U.S. PATENT DOCUMENTS

| | | | |
|---|---|---|---|
| 4,048,342 | A | 9/1977 | Haas et al. |
| 4,049,835 | A | 9/1977 | Haas et al. |
| 4,310,560 | A | 1/1982 | Doster et al. |
| 4,664,922 | A | 5/1987 | Leon et al. |
| 4,804,552 | A | 2/1989 | Ahmed et al. |
| 4,919,960 | A | 4/1990 | Ahmed et al. |
| 5,232,726 | A | 8/1993 | Clark et al. |
| 5,393,547 | A | 2/1995 | Balaban et al. |
| 5,520,943 | A | 5/1996 | Osajima et al. |
| 5,667,835 | A | 9/1997 | Osajima et al. |
| 5,704,276 | A | 1/1998 | Osajima et al. |
| 5,869,123 | A | 2/1999 | Osajima et al. |

OTHER PUBLICATIONS

Arreola, A.G. et al., "Supercritical carbon dioxide effects on some quality attributes of single strength orange juice", J. of Food Science, vol. 56, No. 4, pp. 1030–1033 (1991) (abstract).

Ishikawa, H. et al., "Sterilization of microorganisms by the supercritical carbon dioxide micro–bubble method", Bioscience, Biotechnology and Biochemistry, vol. 59, No. 10, pp. 1949–1950 (1995).

Yun, H. et al., "Effect of a combined treatment of high hydrostatic pressure and carbonation on the quality characteristics of Valencia orange juice", Korean J. of Food Science and Technology, 29(5), pp. 974–981 (1997) (abstract).

Balaban, M.O. et al., "Enzyme Inactivation by Pressurized Carbon Dioxide", Science for the Food Industry of the $21^{st}$ Century (Yalpani, M. ed., ATL Press), pp. 239–251 (1993).

Arreola, A.G. et al., "Effect of Supercritical Carbon Dioxide on Microbial Populations in Single Strength Orange Juice", J. of Food Quality, 14, pp. 275–284 (1991).

CA, Tan et al., vol. 97, p. 180442e (1982).

CA, Pichard et al., vol. 102, p. 91875c (1985).

CA, Crouzet et al., vol. 105, p. 77759y (1986).

CA, Kramer et al., vol. 93, p. 148368s (1980).

CA, Taniguchi et al., vol. 105, p. 113696m (1986).

Abstract, No. 381, "Nonthermal inactivation of pectinesterase from orange juice", 1987, Institute of Food Technologists Annual Meeting (Jun. 16–19, 1987).

Owusu–Yaw et al., "Low pH Inactivation of Pectinesterase in Single Strength Orange Juice", J. Food Sci., vol. 53, pp. 504–507 (1988).

Fife et al., "The Effect of Carbon Dioxide Upon the pH and Certain Nitrogen Fractions of the Sugar–Beet Plant", pp. 643–655 (1935).

Van Slyke et al., "Effect of Treating Milk with Carbon Dioxide Gas Under", New York Agricultural Experiment Station, Bulletin No. 292, pp 371–384 (Aug. 1907).

King et al., "Preservation of raw milk by the addition of carbon dioxide", Journal of Diary Research, 49, pp. 439–447 (1982).

Mabbit, "Preservation of refrigerated milk", National Institute for Research in Dairying, Shinfield, Reading, England, Kieler Milchwirtschaftliche Forschungsberichte 34(1) pp. 28–31 (1982).

King et al., "The Use of Carbon Dioxide for the Preservation of Milk", Society for Applied Bacteriology, Series #22, pp. 35–43 (1987).

Rowe, "Effect of carbon dioxide on growth and extracellular enzyme production by Pseudomonas fluorescens B52", International Journal of food Microbiology, 6, pp. 51–56 (1988).

Rowe, "Carbon dioxide to proling the safe storage of raw milk", Milk Industry 91(7), pp. 17–19 (1989).

Chen et al., "Effect of Dissolved Carbon Dioxide on the Growth of Psychrotrophic Organisms in Cottage Cheese", Journal of Dairy Science, 86 Annual Meeting Am. Diary Science Ass., 74, pp. 2941–2945 (1991).

Maniar et al., "Modified Atmosphere Packaging to Maintain Direct–Set Cottage Cheese Quality", Journal of Food Science, vol. 59, No. 6, pp. 1305–1308 (1994).

Hotchkiss et al., "Extending shelf–life of dairy products with dissolved carbon dioxide", European Dairy Magazine, No. 3, pp. 16, 18–19 (1996).

Goraki, "Commitment to Cottage Cheese", Dairy Foods Ingredient Technology Lab Talk, p. 29, Apr. (1996).

METHOD AND APPARATUS FOR CONTINUOUS FLOW REDUCTION OF MICROBIAL AND/OR ENZYMATIC ACTIVITY IN A LIQUID PRODUCT USING CARBON DIOXIDE

This application is a continuation of U.S. patent application Ser. No. 09/613,714, filed Jul. 11, 2000, now abandoned, which is a continuation-in-part of U.S. patent application Ser. No. 09/314,945, filed May 20, 1999, now abandoned, and claims priority from U.S. provisional application Ser. No. 60/095,967 filed Aug. 10, 1998.

FIELD OF THE INVENTION

This invention relates to a method and apparatus for the processing of liquids to reduce microbial and/or enzymatic activity therein and, more particularly, to the use of carbon dioxide to achieve reductions of microbial and/or enzymatic activity.

BACKGROUND OF THE INVENTION

There are many methods for improving the shelf life of liquid products such as orange juice, apple juice, milk, latex paints, peanut butter, soup, etc.

Commercially, thermal methods such as pasteurization are the predominant methods used to improve the shelf life of liquid foods. Ultra-high pressure treatment is also used for liquid foods, but less frequently.

In high pressure treatment facilities, fluids containing microbial contamination are pressurized hydrostatically to kill the majority of the bacteria. In such systems, pressures are created which equal or exceed 30,000 psia and commonly range from 60,000 to 120,000 psia. Such hydrostatic treatment, however, is unsafe because of the very high pressures, is a lengthy process, is batch rather than continuous, and is expensive due to the high capital costs of the required equipment.

Other methods for shelf-life extension of liquids include nuclear irradiation, ultra-violet exposure and application of microwaves. These treatments are expensive and not widely used commercially at present.

High pressure homogenization has been used to increase the shelf life of orange juice and other single-strength citrus juices as described in U.S. Pat. No. 5,232,726 to Clark et al. It is disclosed that a citrus juice being processed is subjected to a high pressure of about 15,000 psia, with the result being a significant reduction in biological activity in the juice.

Carbon dioxide has been used to inactivate enzymes in food and reduce microbial populations in fruit juices as described in U.S. Pat. No. 5,393,547 to Balaban et al. Balaban et al. describe a method for inactivating enzymes in liquid food products wherein the food is exposed to pressurized carbon dioxide which, in turn, produces a carbonic acid solution with a pH that is sufficiently low to irreversibly inactivate enzymes in the liquid food. The Balaban et al. method is indicated as being applicable to either batch mode or continuous flow mode processing of food. Balaban et al. further indicate that supercritical carbon dioxide is introduced at a rate sufficient to allow enough thereof to dissolve in the food to inactivate the enzymes. After enzymatic inactivation, the food flows to a section where pressure is reduced and the released carbon dioxide may be recycled for repeat usage.

U.S. Pat. No. 5,704,276 to Osajima et al. describes a method for continuous deactivation of enzymes in liquid foodstuffs, using a supercritical form of carbon dioxide. Osajima et al. indicate that the density of the supercritical fluid is less than that of the liquid food and that the supercritical carbon dioxide is injected continuously into the liquid food and is separated therefrom in a later stage of the process. Osajima et al. also indicate that their process deodorizes the liquid food and removes volatile components.

Arreola et al. in "Effect of Supercritical Carbon Dioxide on Microbial Populations in Single Strength Orange Juice", Journal of Food Quality, Volume 14 (1991), pp. 275–284, describe the effect of supercritical carbon dioxide on microbial populations in orange juice. Using a batch process, Arreola et al. concluded that high pressure carbon dioxide treatment resulted in microbial reduction in single strength orange juice, even at low temperatures. Further, they conclude that a combination of high pressure, and shear forces to which the orange juice is subjected during depressurization and lower pH due to temporary formation of carbonic acid may have further inhibitory effects on the normal flora within orange juice. During the processing described in this paper, the minimum temperature utilized was 35° C.

It is an object of this invention to provide an improved method and apparatus for reducing microbial and/or enzymatic activity in liquid products.

It is a further object of this invention to provide a method and apparatus for reducing microbial and/or enzymatic activity in liquid products using pressurized carbon dioxide, wherein the processing temperature to which the liquid is subjected does not deleteriously affect the liquid products.

It is yet another object of this invention to provide a continuous flow method and apparatus for reducing microbial and/or enzymatic activity in liquid products using pressurized carbon dioxide.

SUMMARY OF THE INVENTION

A continuous method using a pressurized flow of carbon dioxide is described for the reduction of microorganisms present in the liquid product and/or the inactivation of one or more enzymes in a pressurized flow of the liquid product. In one embodiment, the pressure in the flow regions is maintained at a level which is sufficient to keep the carbon dioxide in dense phase, but at a temperature which does not freeze the liquid product. In another embodiment, gaseous carbon dioxide is injected directly into the liquid product, forming a mixture which is thereafter pressurized.

The pressurized mixture of the carbon dioxide and liquid flows through a reaction zone for a sufficient time to reduce harmful microorganisms and inactivate enzymes and then enters one or a plurality of expansion stages wherein the pressure of the mixture flow is decreased sufficiently to allow the separation of carbon dioxide from the liquid product. Heat is applied if necessary, to the extent necessary, in at least some of the expansion stages to prevent a cooling of the mixture flow to the freezing point of the liquid product. If heat is applied, the temperature should preferably be controlled so that the liquid does not exceed a temperature at which deleterious effects are experienced. (Freezing and excessive high temperature can have negative effects on the juice quality. Temperatures over 40° C. begin to degrade the product.)

The present invention is contemplated for use with any fluid that may be transported through a conduit, including for example, beverage products such as juices and milk, semi-liquid foods such as mayonnaise, salad dressings, soup and cottage cheese, and other fluids such as paint and sterile injectibles.

DETAILED DESCRIPTION OF THE INVENTION

Figure 1:
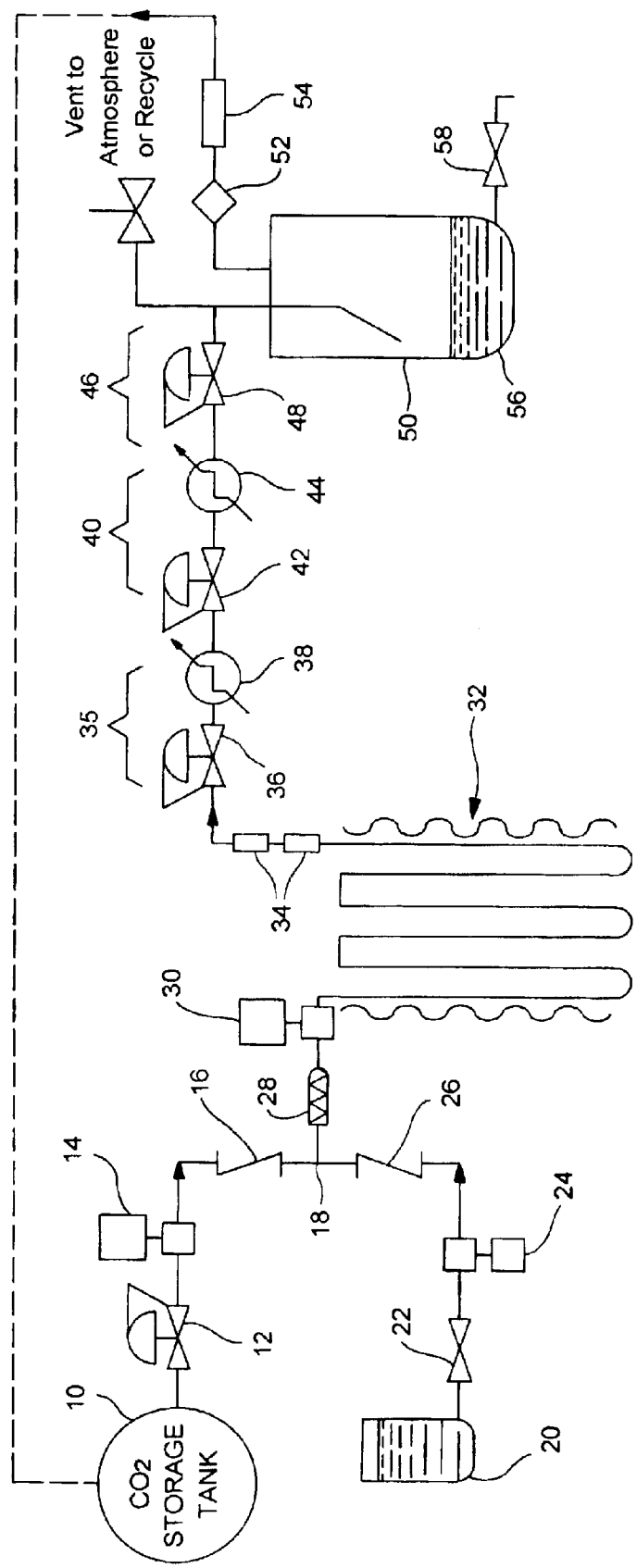
FIG. 1 is a schematic flow diagram of apparatus which performs one embodiment of the invention.

Referring to FIG. 1, pressurized carbon dioxide is fed from carbon dioxide supply 10 through optional pressure regulator 12 to a pump 14 which increases the pressure of the carbon dioxide flow and then feeds it through a check valve 16 to a juncture 18. The carbon dioxide is pressurized at pump 14 to prevent any boiling of the dense phase carbon dioxide during later stages of the process.

In similar fashion, liquid product is fed from a liquid product feed tank 20 through a valve 22 to a pump 24. Pump 24 raises the feed pressure of the liquid product to the same level as that of the dense phase carbon dioxide exiting from pump 14. The pressurized liquid product feed passes through check valve 26 to juncture 18 where it combines with the pressurized flow of carbon dioxide. The mixture of the liquid product and carbon dioxide then passes to an in-line mixer 28 (optional) which essentially comprises a heavily baffled conduit that thoroughly mixes the carbon dioxide and liquid product streams. Of course, other mixers may be employed which achieve a desired level of liquid product/carbon dioxide mixing. The liquid mixture exits from in-line mixer 28 and is further pressurized by the action of pump 30 to a process pressure.

Depending upon the specific liquid product feed, the process pressure will vary accordingly. It is preferred that the process pressure be within the range of 300 psia to 20,000 psia. If orange juice is being processed as a liquid food, a preferred range of pressure is about 3000 psia to about 7000 psia.

Figure 2:
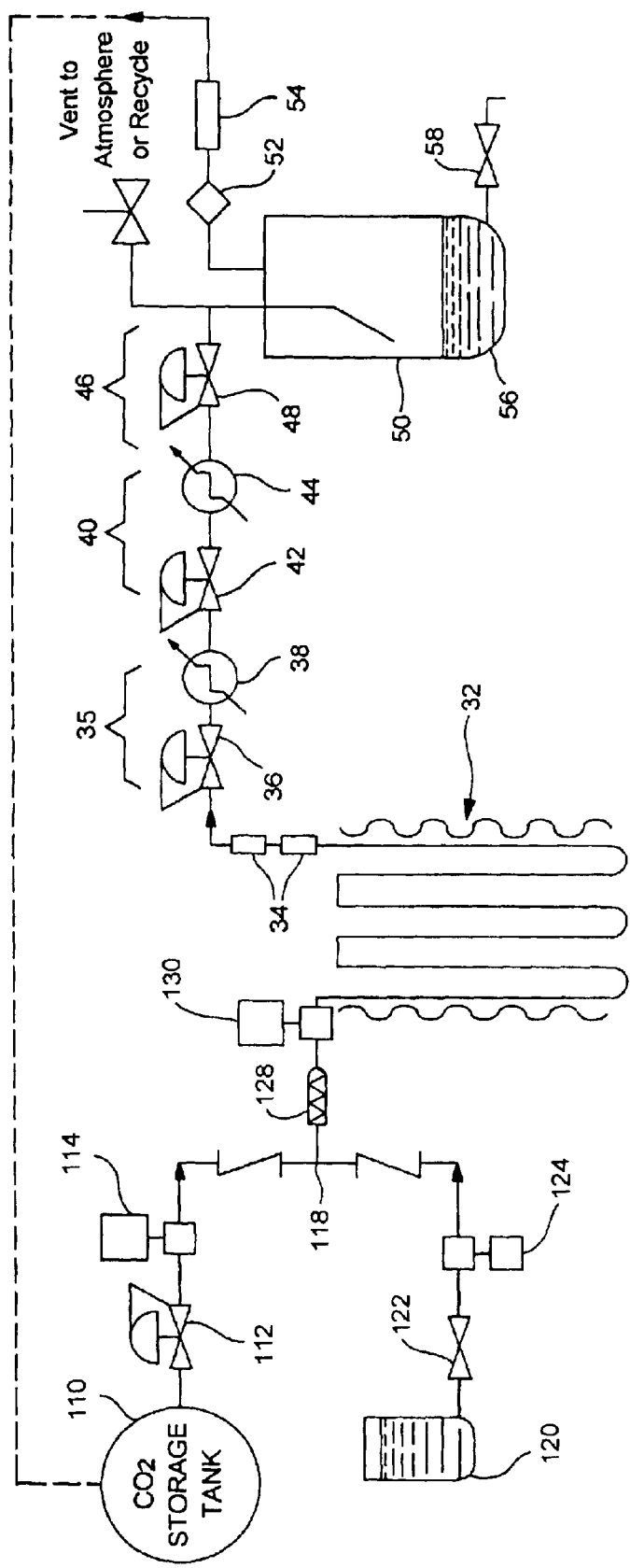
FIG. 2 is a schematic flow diagram of apparatus which performs another embodiment of the invention.

Referring to FIG. 2, carbon dioxide is fed from source 110 through optional pressure regulator 112. Pump 114 can pressurize the carbon dioxide to dense phase or liquid and convey it to juncture 118, or if the carbon dioxide is gaseous then pump 114 can be omitted and the gas flows under its own pressure to juncture 118. Separately, liquid product is fed from liquid product feed tank 120 through valve 122. Preferably, a pump 124 helps convey the liquid product to juncture 118 but need not pressurize the liquid product.

The liquid product and the carbon dioxide are mixed together, in-line (for instance at juncture 118) or for instance with the aid of optional mixing device 128 (which could be at juncture 118). If the carbon dioxide is liquid, an in-line mixer or equivalent device can be used as described with respect to device 28 in FIG. 1. If the carbon dioxide is gaseous, any device effective to feed the gas into the liquid product can be used, such as a sparger, in-line injector, sidestream injection, ultrasonic transducers, or mixing with dry ice. Injection devices include membranes, sintered metal spargers, flexible diffusers, sidestream ejectors, venturi injectors, and equivalent ("Praso") valves. The gaseous carbon dioxide can be fed into the feed line through which the liquid product passes, or into a holding tank (not shown) located at a point in the feed line between juncture 118 and pump 130. Then the mixture is pressurized at pump 130 to process pressure.

Once the liquid mixture however formed exits from pump 30 or 130, it enters a reaction zone 32 that is of suitable size and length to provide sufficient contact (or residence) time for the carbon dioxide and liquid product to interact in a manner which reduces microorganisms and/or inactivates enzymes including undesirable enzymes present in the liquid product. The selected residence time will depend on the liquid product to be processed and its flowrate, as well as the size and length of the reaction zone. It is preferred that the reaction zone residence time is in the range of about 1.0 to about 15.0 minutes.

For example, for processing orange juice, at a flowrate of 500 ml/min in a reaction zone having a length of about 100 feet and tubing size of about 0.56 inches (142 mm) inner diameter (I.D.), the preferred residence time is about 1.5 to 13.0 minutes, and more preferably about 3.0 minutes of residence time.

As the liquid mixture stream exits from reaction zone 32, it enters one or more interaction chambers 34 (optional) wherein high shear forces are applied which enable a rupture of microbial cell walls in the liquid mixture. Such action enables a further reduction of the microbial populations in the liquid mixture. For example, a high shear interaction chamber can be used, one example of which suitable for inclusion in this process is manufactured by the Microfluidics International Corp., Newton, Mass. Homogenizers are also useful for this purpose.

At this stage, the pressurized carbon dioxide/liquid product mixture must be depressurized in such a fashion as to avoid freezing the liquid product (due to the Joule-Thompson cooling effect of the expansion of the carbon dioxide). If the pressure is lowered to ambient in one or two stages, application of supplemental heat may be required. If too much heat is added to the mixture, damage will occur to the liquid product, either in its flavor characteristics or its composition. Also, important volatiles such as flavor components may be carried away. Accordingly, it has been found that substantial care must be taken during the depressurization action to maintain the liquid mixture within two boundaries. The lower boundary is the freezing point of the liquid mixture and the upper boundary point is the maximum temperature to which the liquid product can be subjected, without damage to the product.

In the case of orange juice, the maximum temperature is about 60° C. and the minimum temperature is about 0° C. Accordingly, when choosing a pressure reduction scheme, a pressure/enthalpy chart for carbon dioxide is followed to determine the optimum pressure and heating temperature needed for plural pressure reduction stages, while keeping (in this example) the orange juice at a temperature between that which will injure its flavor and its freezing point. It has been determined that at least two stages of depressurization are preferred, but one or multiple stages are possible.

Returning to FIG. 1, while one or more depressurization stages can be used, three are shown. The first depressurization stage includes a pressure control device 36, such as a back pressure regulator, followed by a heat exchanger 38. Assuming that the liquid product being processed is orange juice and that the process pressure within reaction zone 32 and (optional) interaction chamber 34 is about 5,000 psig, a first depressurization stage 35 reduces the pressure of the liquid mixture to approximately 500 psig and applies sufficient heat through heat exchanger 38 to maintain the liquid mixture at about 20° C.

A second optional depressurization stage 40 includes a pressure control device 42 and heat exchanger 44 which, in combination, reduce the pressure of the liquid mixture to about 250 psia and maintains its temperature at approximately 30° C. A final stage depressurizer 46 includes only a pressure control device 48 to reduce the pressure of the liquid mixture to the point where the dense phase carbon dioxide will vaporize and may be separated from the liquid products while minimizing loss of important volatile components. In the embodiment shown in the figure, no heat exchanger is required subsequent to pressure control device 48, however, one may be provided, if required, to maintain the liquid mixture within the required temperature range.

As the liquid mixture exits from pressure control device 48, it enters a liquid product/carbon dioxide separator vessel 50 or other collection device at reduced pressure. There, the carbon dioxide vapor separates from the liquid product, is captured and (if desired) is passed through optional filter 52 and/or optional flow meter 54 and is either vented to atmosphere or is passed through a pressurization stage (not shown) for recycling back to carbon dioxide supply 10. The liquid product pool 56 may then be drained through valve 58 for subsequent processing and/or use. There may be included a stage (not shown) for reducing residual dissolved carbon dioxide to desired levels, e.g. from on the order of 1200 ppm down to 300–400 ppm or less.

It is to be understood, that the continuous process method shown in the figure is made practical by the one or more, preferably multiple, depressurization stages which enable the liquid mixture to be maintained within the aforementioned temperature boundaries. As a result, a continuous process for reduction of microbial and/or enzymatic activity is achieved while overcoming the principal problem of the prior art, i.e., batch processing which is an uneconomic and undesired processing procedure in a commercial environment.

If the carbon dioxide gas is to be recycled, it may be passed through a coalescing filter to remove droplets of the processed liquid product. Thereafter, the gas is recondensed, or compressed, to the liquid state by passage through a condensing heat exchanger or compressor. Further, to assure removal of the dissolved carbon dioxide in the processed liquid product, a liquid product/carbon dioxide separator downstream from separator tank 50 may include means for dissolved gas removal.

The resultant gas, remaining after processing, may carry additional valuable aromas and/or flavors. To recover or remove such aromas or flavors, a method such as condensation or absorption may be utilized.

It should be understood that the foregoing description is only illustrative of the invention. Various alternatives and modifications can be devised by those skilled in the art without departing from the invention.

What is claimed is:

1. A continuous method for reducing one or more of microorganisms or enzymes in a liquid product, said method comprising the steps of:
   a) forming a pressurized mixture by
      i) combining a pressurized flow of said liquid product with a flow of pressurized liquefied carbon dioxide to create a pressurized mixture in a flow state, said carbon dioxide at a pressure sufficient to maintain it in a liquid state and at a temperature which does not freeze said liquid product; or
      ii) forming a mixture of said liquid product with liquid or gaseous carbon dioxide, wherein said carbon dioxide if in the liquid state is at a pressure sufficient to maintain it in a liquid state and at a temperature which does not freeze said liquid product, and then pressurizing said mixture;
   b) flowing said pressurized mixture through a reaction zone for a sufficient time to reduce at least one of said microorganisms and said enzymes in said liquid mixture;
   c) feeding said pressurized mixture from said reaction zone through one or more expansion stages wherein the pressure of said mixture flow is decreased to vaporize the carbon dioxide in said mixture; and
   d) applying heat in at least one of said expansion stages to said mixture if necessary, to the extent necessary, to prevent cooling of said carbon dioxide from causing freezing of said liquid product.

2. The continuous method as recited in claim 1, wherein step a) comprises combining a pressurized flow of said liquid product with a flow of pressurized liquefied carbon dioxide to create a pressurized mixture in a flow state, said carbon dioxide at a pressure sufficient to maintain it in a liquid state and at a temperature which does not freeze said liquid product.

3. The continuous method as recited in claim 2, wherein in step d) heat is applied to said mixture in at least one of said expansion stages.

4. The continuous method as recited in claim 3, wherein step d) maintains the temperature of said mixture within a range between the freezing temperature of said liquid product and about 60° C.

5. The continuous method as recited in claim 2, wherein step c) feeds said mixture flow through two or more expansion stages to vaporize said liquefied carbon dioxide.

6. The continuous method as recited in claim 2, wherein step a) feeds said pressurized flow of said mixture in said reaction zone at a pressure within a range of about 300 psia to about 20,000 psia.

7. The continuous method as recited in claim 2, wherein step b) maintains said pressurized flow of said mixture in said reaction zone for a duration of from about 5 seconds to about 30 minutes.

8. A continuous method as recited in claim 1, wherein step a) comprises forming a mixture of said liquid product with liquid or gaseous carbon dioxide, wherein said carbon dioxide if in the liquid state is at a pressure sufficient to maintain it in a liquid state and at a temperature which does not freeze said liquid product, and then pressurizing said mixture.

9. The continuous method as recited in claim 8, wherein in step d) heat is applied to said mixture in at least one of said expansion stages.

10. The continuous method as recited in claim 9, wherein step d) maintains the temperature of said mixture within a range between the freezing temperature of said liquid product and about 60° C.

11. The continuous method as recited in claim 8, wherein step c) feeds said mixture flow through two or more expansion stages to vaporize said liquefied carbon dioxide.

12. The continuous method as recited in claim 8, wherein step a) feeds said pressurized flow of said mixture in said reaction zone at a pressure within a range of about 300 psia to about 20,000 psia.

13. The continuous method as recited in claim 8, wherein step b) maintains said pressurized flow of said mixture in said reaction zone for a duration of from about 5 seconds to about 30 minutes.

14. A continuous method for reducing microorganisms and inactivating one or more enzymes in liquid juice product, said method comprising the steps of:
   a) forming a pressurized mixture by
      i) combining a pressurized flow of said liquid juice product with a flow of pressurized liquefied carbon dioxide to create a pressurized mixture in a flow state, said carbon dioxide at a pressure sufficient to maintain it in a liquid state and at a temperature which does not freeze said liquid juice product; or ii) forming a mixture of said liquid juice product with liquid or gaseous carbon dioxide, wherein said carbon dioxide if in the liquid state is at a pressure sufficient to maintain it in a liquid state and at a temperature which does not freeze said liquid juice product, and then pressurizing said mixture;

b) flowing said pressurized mixture through a reaction zone for about 1.0 to about 15 minutes to reduce said microorganisms present therein and inactivate said one or more enzymes;

c) feeding said pressurized mixture from said reaction zone through one or more expansion stages wherein the pressure of said mixture flow is decreased; and d) applying heat in at least one of said expansion stages to said mixture flow if necessary, to the extent necessary, to prevent cooling of said carbon dioxide from causing freezing of said liquid juice product.

15. The continuous method as recited in claim 14, wherein the juice is a vegetable or fruit juice and wherein the contact time in step b) is about 1.5 to about 13 minutes.

16. The continuous method as recited in claim 14, wherein step d) maintains the temperature of said mixture within a range between the freezing temperature of said liquid juice product and about 30° C.

17. The continuous method as recited in claim 14, wherein said juice is orange juice, said contact time is about 3.0 minutes, and wherein step d) maintains the temperature of said mixture at about 30° C.

18. The continuous method as recited in claim 17, wherein step a) feeds said pressurized flow of said mixture in said reaction zone at a pressure of about 5,000 psia.

19. Apparatus for performing a continuous method of reducing microorganisms in a liquid product, said apparatus comprising:

a) means for providing a pressurized mixture, comprising either
   i) pump means for providing a pressurized flow of said liquid product and liquefied carbon dioxide and for creating a pressurized mixture thereof in a flow state, said pump means pressurizing said carbon dioxide to a pressure that is sufficient to maintain it in a liquid state but at a temperature that does not freeze said liquid product; or
   (ii) means for mixing liquid carbon dioxide with said liquid product, or means for mixing gaseous carbon dioxide with said liquid product, and means for pressuring the resultant mixture;

b) reaction zone means for receiving said pressurized mixture in a continuous flow state, and for enabling a residence time therein of said pressurized mixture that is sufficient to allow said carbon dioxide to reduce microorganisms in said liquid product;

c) one or more expansion devices for receiving said pressurized mixture flow from said reaction zone means, each expansion device configured to enable a reduction of the pressure of said mixture flow, so as to allow said mixture flow to exit said one or more expansion devices at a desired exit pressure; and d) heat exchange means for applying heat to said liquid mixture in at least one of said expansion devices if necessary, to the extent necessary, to prevent cooling of said carbon dioxide therein and causing freezing of said liquid product.

20. The apparatus as recited in claim 19, wherein said heat exchange means maintains a temperature of said mixture within a range between the freezing temperature of said liquid product and 60° C.

21. The apparatus as recited in claim 19, wherein said plural expansion devices consist of two or more expansion devices and said exit pressure is ambient.

22. The apparatus as recited in claim 19, wherein said pump means feeds said pressurized flow of said mixture into said reaction zone means at a pressure within a range of about 300 psia to about 20,000 psia.

23. The apparatus as recited in claim 19, wherein said reaction zone means provides a residence time, for said pressurized flow of said mixture, of a duration of from about 5 seconds to about 30 minutes.

24. The apparatus as recited in claim 19, wherein said liquid product is orange juice and said heat exchange means maintains a temperature of said mixture within a range between the freezing temperature of said orange juice and 30° C.

25. The apparatus as recited in claim 24, wherein said plural expansion devices consist of two or more expansion devices and said exit pressure is between about 250 psia to about 850 psia.

26. The apparatus as recited in claim 25, wherein said pump means feeds said pressurized flow of said mixture into said reaction zone means at a pressure of about 5,000 psia.

27. The apparatus as recited in claim 24, wherein said reaction zone means provides a residence time, for said pressurized flow of said mixture, of a duration of about 3 minutes.

28. A continuous method for reducing microorganisms in a liquid product, said method comprising the steps of:

a) combining a pressurized flow of said liquid product with a flow of pressurized liquefied carbon dioxide to create a pressurized mixture in a flow state, said carbon dioxide at a pressure sufficient to maintain it in a liquid state and at a temperature which does not freeze said liquid product;

b) flowing said pressurized mixture through a reaction zone for a sufficient time to reduce microorganisms in said liquid product;

c) feeding said pressurized mixture from said reaction zone through plural expansion stages wherein the pressure of said mixture flow is decreased to vaporize the liquefied carbon dioxide in said mixture flow; and d) applying heat in at least some of said expansion stages to said mixture flow to prevent a cooling of said carbon dioxide from causing a freezing of said liquid product.

29. The continuous method as recited in claim 28, wherein step d) maintains a temperature of said mixture within a range between a freezing temperature of said liquid product and about 60° C.

30. The continuous method as recited in claim 28, wherein step c) feeds said mixture flow through two or more expansion stages to vaporize said liquefied carbon dioxide.

31. The continuous method as recited in claim 28, wherein step a) feeds said pressurized flow of said mixture in said reaction zone at a pressure within a range of about 300 psia to about 20,000 psia.

32. The continuous method as recited in claim 28, wherein step b) maintains said pressurized flow of said mixture in said reaction zone for a duration of from about 5 seconds to about 30 minutes.

33. The continuous method as recited in claim 28, wherein said liquid product is a food product and said method inactivates one or more enzymes.

34. A continuous method for reducing microorganisms and inactivating one or more enzymes in liquid juice product, said method comprising the steps of:

a) combining a pressurized flow of said liquid juice product with a flow of pressurized liquefied carbon dioxide to create a pressurized mixture in a flow state, said carbon dioxide at a pressure sufficient to maintain it in a liquid state and at a temperature which does not freeze said liquid juice product;

b) flowing said pressurized mixture through a reaction zone for about 1.0 to about 15 minutes to reduce said microorganisms present therein and inactivate said one or more enzymes;

c) feeding said pressurized mixture from said reaction zone through two or more expansion stages wherein the pressure of said mixture flow is decreased to about 2,000 psia; and d) applying heat in at least some of said expansion stages to said mixture flow to prevent a cooling of said carbon dioxide from causing a freezing of said liquid juice product.

35. The continuous method as recited in claim 34, wherein the juice is a vegetable or fruit juice and wherein the contact time in step b) is about 1.5 to about 13 minutes.

36. The continuous method as recited in claim 34, wherein step d) maintains a temperature of said mixture within a range between a freezing temperature of said liquid juice product and about 30° C.

37. The continuous method as recited in claim 35, wherein said juice is orange juice, said contact time is about 3.0 minutes, and wherein step d) maintains a temperature of said mixture at about 30° C.

38. The continuous method as recited in claim 37, wherein step a) feeds said pressurized flow of said mixture in said reaction zone at a pressure of about 5,000 psia.

39. Apparatus for performing a continuous method of reducing microorganisms in a liquid product, said apparatus comprising:

a) pump means for providing a pressurized flow of said liquid product and liquefied carbon dioxide and for creating a pressurized mixture thereof in a flow state, said pump means pressurizing said carbon dioxide to a pressure that is sufficient to maintain it in a liquid state but at a temperature that does not freeze said liquid product;

b) reaction zone means for receiving said pressurized mixture in a continuous flow state, and for enabling a residence time therein of said pressurized mixture that is sufficient to allow said carbon dioxide to reduce microorganisms in said liquid product;

c) plural expansion stages for receiving said pressurized mixture flow from said reaction zone, each expansion device configured to enable a reduction of the pressure of said mixture flow, so as to allow said mixture flow to exit said plural expansion stages at a desired exit pressure; and d) heat exchange means for applying heat to said liquid mixture in at least some of said expansion devices to prevent a cooling of said carbon dioxide therein and causing a freezing of said liquid product.

40. The apparatus as recited in claim 39, wherein said heat exchange means maintains a temperature of said mixture within a range between a freezing temperature of said liquid product and 60° C.

41. The apparatus as recited in claim 39, wherein said plural expansion devices consist of two or more expansion devices and said exit pressure is ambient.

42. The apparatus as recited in claim 39, wherein said pump means feeds said pressurized flow of said mixture into said reaction zone means at a pressure within a range of about 300 psia to about 20,000 psia.

43. The apparatus as recited in claim 39, wherein said reaction zone means provides a residence time, for said pressurized flow of said mixture, of a duration of from about 5 seconds to about 30 minutes.

44. The apparatus as recited in claim 39, wherein said liquid product is orange juice and said heat exchange means maintains a temperature of said mixture within a range between a freezing temperature of said orange juice and 30° C.

45. The apparatus as recited in claim 44, wherein said plural expansion devices consist of two or more expansion devices and said exit pressure is between about 350 psia to about 850 psia.

46. The apparatus as recited in claim 45, wherein said pump means feeds said pressurized flow of said mixture into said reaction zone means at a pressure of about 5,000 psia.

47. The apparatus as recited in claim 44, wherein said reaction zone means provides a residence time, for said pressurized flow of said mixture, of a duration of about 3 minutes.

* * * * *